(12) United States Patent
Sakai et al.

(10) Patent No.: US 8,354,133 B2
(45) Date of Patent: Jan. 15, 2013

(54) MODIFYING AGENT FOR PLASTIC FAT

(75) Inventors: Midori Sakai, Hyogo (JP); Masayuki Murayama, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 13/264,714

(22) PCT Filed: Apr. 2, 2010

(86) PCT No.: PCT/JP2010/056086
§ 371 (c)(1),
(2), (4) Date: Oct. 14, 2011

(87) PCT Pub. No.: WO2010/119781
PCT Pub. Date: Oct. 21, 2010

(65) Prior Publication Data
US 2012/0040077 A1   Feb. 16, 2012

(30) Foreign Application Priority Data
Apr. 16, 2009   (JP) .................... 2009-099946

(51) Int. Cl.
*A23D 9/00* (2006.01)
(52) U.S. Cl. .............. 426/607; 426/601; 426/606
(58) Field of Classification Search ............ 426/601, 426/606, 607
See application file for complete search history.

(56) References Cited

U.S. PATENT DOCUMENTS

| | | | |
|---|---|---|---|
| 5,142,071 A | 8/1992 | Kluesener et al. | |
| 5,395,629 A | 3/1995 | Bertoli et al. | |
| 5,888,575 A * | 3/1999 | Lansbergen et al. | 426/610 |
| 2008/0260931 A1 * | 10/2008 | Arimoto et al. | 426/607 |

FOREIGN PATENT DOCUMENTS

| | | |
|---|---|---|
| JP | 63-317585 A | 12/1988 |
| JP | 02-001799 A | 1/1990 |
| JP | 04-075593 A | 3/1992 |
| JP | 5-502668 | 5/1993 |
| JP | 06-209705 A | 8/1994 |
| JP | 10-183165 A | 7/1998 |
| JP | 2000-212590 A | 8/2000 |
| JP | 2002-038191 A | 2/2002 |
| WO | WO-91/09099 A1 | 6/1991 |
| WO | WO-98/19554 A1 | 5/1998 |
| WO | WO-2006/121182 A1 | 11/2006 |

OTHER PUBLICATIONS

International Search Report issued in International Application No. PCT/JP2010/056086.
PCT International Preliminary Report of Patentability issued in International Application No. PCT/JP2010/056086 and Translation of PCT Written Opinion of the International Searching Authority, date of mailing Jul. 6, 2010.

* cited by examiner

*Primary Examiner* — Carolyn Paden
(74) *Attorney, Agent, or Firm* — Connolly Bove Lodge & Hutz LLP

(57) ABSTRACT

Provided are a modifying agent for a plastic fat to be used in a plastic fat comprising palm oil, which inhibits changes in physical properties of the plastic fat such as hardness or crude crystal formation and gives an air-containing plastic fat; and a plastic fat using the same. A plastic fat is prepared by using, as modifying agent, an appropriate amount of a fat composition which comprised triglycerides comprising, as constituting fatty acids, a saturated fatty acid (A) having a melting point of 60° C. or higher and a saturated fatty acid (B) having a melting point of 40° C. or lower, wherein the fat composition contains 40-85 wt %, relative to the total fat composition, of ABB type triglycerides, and the weight ratio (ABB/AAB) of said ABB type triglycerides o AAB type triglycerides is 2-15.

3 Claims, No Drawings

MODIFYING AGENT FOR PLASTIC FAT

CROSS REFERENCE TO RELATED APPLICATIONS

This application is a National Phase filing under 35 U.S.C. §371 of PCT/JP2010/056086, filed on Apr. 16, 2010; and this application claims priority to Application No. 2009-099946, filed in Japan on Apr. 16, 2009 under 35 U.S.C. §119; the entire contents of all are hereby incorporated by reference.

TECHNICAL FIELD

The present invention relates to modifying agents used for plastic fats such as margarine and shortening including palm oil as a main material.

BACKGROUND ART

Conventionally, hydrogenated fats such as hardened fish oil and vegetable oil have been used as raw materials for plastic fats because such a fat can provide good physical properties and functions. However, in recent years, the use of the hydrogenated fats has been limited because the hydrogenated fats contain trans-fatty acids that cause human heart diseases, and thus the replacement of the hydrogenated fats with palm oil and the like is recommended.

It is known that the combination of the palm oil as a main material in the plastic fat such as margarine and shortening is apt to cause changes such as the formation of coarse crystals and the increase in hardness during storage or distribution, and also, is not able to provide a plastic fat that can highly contain air. Hence, a triglyceride structure in the palm oil has been modified by transesterification.

For example, Patent Document 1 discloses a fat composition that can suppress quality change over time by mixing palm oil or palm stearin and a fat containing lauric acid in a certain fatty acid ratio and transesterifying the mixture. Furthermore, Patent Document 2 discloses a fat composition capable of producing a plastic fat that can eliminate the formation of coarse crystals and lead to a few changes over time by transesterifying a liquid vegetable oil containing a palm-based fat and unsaturated fatty acids in large amounts to make a component ratio of dipalmitoyl monooleoyl glyceride PPO/POP$\geqq$0.5 (P: palmitic acid, O: oleic acid). These modifying methods change the triglyceride POP in the palm oil into other components and achieve a certain effect on the suppression of the changes over time, but the effect is insufficient. These methods have another problem. For example, the methods simultaneously form tri-saturated triglycerides having a high melting point to reduce solubility in a mouth.

There are also disclosed methods for improving qualities of a plastic fat and chocolate that contain palm oil by using a fat composition that specifies the type or bonding site of a fatty acid constituting triglycerides. For example, Patent Document 3 discloses a fat composition that can prominently increase the crystallization rate by incorporating an XXM type triglyceride (X: a C>15 saturated chain, M: a C<15 saturated chain) in a small amount into a fat that has a low crystallization rate and is a low trans-fatty acid, such as the palm oil. Patent Document 4 discloses that a 1,3-di(S)-2-mono(X) type triglyceride (SXS) bonded with a saturated fatty acid (X) having 12 or less carbon atoms at the 2-position and bonded with saturated fatty acids (S) each having 16 or more carbon atoms at the 1- and 3 positions can suppress bloom of chocolate. These methods are effective on the suppression of coarse crystal formation in a plastic fat and the suppression of the bloom of chocolate, but have small suppressive effect on the changes over time.

In recent years, a low-calorie fat has been drawing attention as a health functional fat, and there are disclosed some triglycerides containing, in a molecule, a saturated long chain fatty acid having 16 or more carbon atoms and a medium chain fatty acid having 10 or less carbon atoms (for example, Patent Document 5 and Patent Document 6).

Furthermore, Patent Document 7 discloses an intermolecular compound of (a) a di-saturated medium chain fatty acid mono-long chain fatty acid triglyceride and (b) a 1,3-disaturated long chain fatty acid 2-monounsaturated long chain fatty acid triglyceride, and the intermolecular compound has a longer interplanar spacing of 65 Å or more as determined by X-ray diffraction. It is described that the intermolecular compound can maintain a smooth texture of chocolate containing cacao butter in a large amount and can suppress the formation of bloom. Moreover, it is described that the intermolecular compound is also effective for the suppression of the hardness change of a plastic fat over time. The literature discloses no specific method for use of the plastic fat. However, it is not easy to obtain a composition that contains the di-saturated medium chain fatty acid mono-long chain fatty acid triglyceride at a high concentration, which can provide the intermolecular compound having a longer interplanar spacing of 65 Å or more as determined by X-ray diffraction. Moreover, the presence of the di-saturated medium chain fatty acid mono-long chain fatty acid triglyceride in an equimolar amount to that of the 1,3-disaturated long chain fatty acid 2-monounsaturated long chain fatty acid triglyceride softens the plastic fat too much or lead to a lower melting point. Therefore, it is not preferred to use the intermolecular compound for margarine and shortening as a main material.

CITATION LIST

Patent Literature

Patent Document 1: JP-A No. 2000-212590
Patent Document 2: JP-A No. 1998-183165
Patent Document 3: WO 98/19554 pamphlet
Patent Document 4: JP-A No. 1992-75593
Patent Document 5: JP No. 2962730
Patent Document 6: JP-A No. 2002-38191
Patent Document 7: WO 2006/121182 pamphlet

SUMMARY OF INVENTION

Technical Problem

It is an object of the present invention to provide a modifying agent for a plastic fat that has a suppressive effect on physical property changes of a plastic fat using palm oil, such as the change in hardness and the formation of coarse crystals and that can provide a plastic fat having air containing properties, namely, creaming properties.

Solution to Problem

The present inventors have repeatedly carried out intensive studies in order to solve the problems, as a result, have found that, by adding a modifying agent alone in a certain amount to a plastic fat, the modifying agent being composed of a fat composition that includes a triglyceride containing a saturated fatty acid (A) having a melting point of 60° C. or more and a saturated fatty acid (B) having a melting point of 40° C. or less as constituent fatty acids, that contains an ABB type triglyceride bonded with one saturated fatty acid (A) and two saturated fatty acids (B) in a certain amount based on the whole fat composition, and that has a weight ratio (ABB/AAB) of the ABB type triglyceride to an AAB type triglyceride bonded with two saturated fatty acids (A) and one saturated fatty acid (B) of a certain value or more, the plastic fat obtains physical properties in which the changes are suppressed, a hardness that is unlikely to be changed, and creaming properties are good, and accordingly the invention has been accomplished.

Namely, a first aspect of the present invention relates to a modifying agent for a plastic fat including a fat composition that includes a triglyceride containing a saturated fatty acid (A) having a melting point of 60° C. or more and a saturated fatty acid (B) having a melting point of 40° C. or less as constituent fatty acids. The fat composition contains an ABB type triglyceride bonded with one saturated fatty acid (A) and two saturated fatty acids (B) in an amount of 40 to 85% by weight based on the whole fat composition, and has a weight ratio (ABB/AAB) of the ABB type triglyceride to an AAB type triglyceride bonded with two saturated fatty acids (A) and one saturated fatty acid (B) of 2 to 15.

In the modifying agent, it is preferred that a C16 to C22 saturated fatty acid (A) is included in an amount of 50 to 70% by weight and a C6 to C10 saturated fatty acid (B) is included in an amount of 30 to 50% by weight in the whole fatty acids constituting the triglyceride.

In the modifying agent, it is further preferred that a C18 saturated fatty acid (A) is included in an amount of 50 to 70% by weight and a C8 to C10 saturated fatty acid (B) is included in an amount of 30 to 50% by weight based on the whole fatty acids constituting the triglyceride.

A second aspect of the present invention relates to a plastic fat that includes the ABB type triglyceride in an amount of 2 to 10% by weight and does not substantially include lauric acid. More specifically, the plastic fat of the present invention includes the modifying agent to contain the ABB type triglyceride in an amount of 2 to 10% by weight based on the whole fat and includes palm oil in an amount of 50 to 98% by weight, and lauric acid is included in an amount of less than 5% by weight.

Advantageous Effects of Invention

According to the present invention, a modifying agent that is used in a plastic fat such as margarine and shortening using palm oil to give a plastic fat having a suppressive effect on the physical property changes such as the change in hardness and the formation of coarse crystals and having air containing properties (namely, creaming properties) can be provided. The present invention can also provide a plastic fat that uses the modifying agent, has a few physical property change such as the change in hardness and the formation of coarse crystals, and has air containing properties.

DESCRIPTION OF EMBODIMENTS

Hereinafter, the present invention will be described in further detail. The modifying agent for a plastic fat of the present invention includes a fat composition that includes a triglyceride containing a saturated fatty acid (A) having a melting point of 60° C. or more and a saturated fatty acid (B) having a melting point of 40° C. or less as constituent fatty acids. The fat composition contains an ABB type triglyceride bonded with one saturated fatty acid (A) and two saturated fatty acids (B) in a certain amount based on the whole fat composition, and has a weight ratio (ABB/AAB) of the ABB type triglyceride to an AAB type triglyceride bonded with two saturated fatty acids (A) and one saturated fatty acid (B) within a certain range. In the description below, the modifying agent for a plastic fat of the present invention is also simply described as "modifying agent".

The saturated fatty acid (A) in the present invention is not specifically limited as long as it is a constituent fatty acid of the triglyceride and has a melting point of 60° C. or more. Examples of the saturated fatty acid (A) include stearic acid (C18), palmitic acid (C16), arachidic acid (C20), and behenic acid (C22). Considering costs and ready availability, the saturated fatty acid (A) is preferably a C18 to C20 fatty acid because a material containing the behenic acid (C22) is expensive.

The saturated fatty acid (B) in the present invention is not specifically limited as long as it is a constituent fatty acid of the triglyceride and has a melting point of 40° C. or less. Examples of the saturated fatty acid (B) include caproic acid (C6), caprylic acid (C8), and capric acid (C10). Considering costs and ready availability, the saturated fatty acid (B) is preferably a C8 to C10 fatty acid because a material containing the caproic acid (C6) is expensive.

In the invention, the determination of the fatty acid composition in the fat composition was performed as follows.

<Determination of Fatty Acid Composition in Fat>

The determination was carried out by capillary gas chromatography with FID detection under isothermal condition. The gas chromatography is a method described in "2. 4. 2. 1 Fatty Acid Composition" in "Standard Methods for the Analysis of Fats, Oils and Related Materials" edited by Japan Oil Chemists Society (published in 1996).

The ABB type triglyceride in the present invention is a triglyceride bonded with one saturated fatty acid (A) and two saturated fatty acids (B), and each fatty acid is bonded to any position. The AAB type triglyceride in the present invention is a triglyceride bonded with two saturated fatty acids (A) and one saturated fatty acid (B), and each fatty acid is bonded to any position. In the description below, the ABB type triglyceride is simply described as "ABB". The AAB type triglyceride is also simply described as "AAB". The meanings of "AAA", "BBB", and the like are alike. Furthermore, for example, "$A_{C18}B_{C8}B_{C8}$" means a triglyceride bonded with one C18 saturated fatty acid (stearic acid) and two C8 saturated fatty acids (caprylic acid).

In the modifying agent composed of the fat composition according to the present invention, the content of ABB in the fat composition is preferably 40 to 85% by weight based on the whole fat composition. The addition of the modifying agent having an ABB content of less than 40% by weight into a plastic fat may not sufficiently achieve the suppressive effect on the physical property changes such as the change in hardness and the formation of coarse crystals in the plastic fat. The modifying agent having an ABB content of more than 85% by weight may not preferred because, for example, such an agent increases the cost for purifying the fat composition as the modifying agent and the ratio ABB/AAB is increased. The ABB content in the modifying agent is determined as follows.

<Determination of ABB Content and AAB Content in Modifying Agent>

In the modifying agent for a plastic fat prepared in the invention, each of the ABB content and the AAB content was determined, by using a gas chromatograph equipped with a capillary column and a hydrogen flame ionization detector, from retention times and peak area ratios in the obtained chart. The measurement conditions are as below.

| Column: | TAP-CB (manufactured by GL Sciences Inc.) ID: 0.2 mm, length: 25 m |
|---|---|
| Oven temp profile: | |
| Initial temp: | 280° C. |
| Initial hold time: | 3 min |
| Program rate: | 4° C./min |
| Final temp: | 360° C. |
| Final hold time: | 5 min |

In the modifying agent composed of the fat composition according to the present invention, the weight ratio (ABB/AAB) of ABB to AAB in the fat composition is preferably 2 to 15, and more preferably 3 to 15. The fat composition having an ABB/AAB ratio of less than 2 may not sufficiently achieve the suppressive effect on the change in hardness of a plastic fat. The fat composition having an ABB/AAB ratio of more than 15, on the other hand, may cause problems in the production, for example, such a composition increases the hardness of a plastic fat, which interferes with operation.

For the production of a plastic fat, the used amount of the modifying agent of the present invention is preferably adjusted so that the content of ABB will be 2 to 10% by weight based on the whole plastic fat. The, plastic fat having an ABB content of less than 2% by weight based on the whole plastic fat may not obtain a sufficient suppressive effect on the physical property changes such as the change in hardness and the formation of coarse crystals in the plastic fat. The plastic fat having an ABB content of more than 10% by weight based on the whole plastic fat may be excessively softened and increases the cost as well.

A method for producing the modifying agent for a plastic fat, of the present invention is exemplified as follows. A component (I) selected from at least one of a fatty acid corresponding to the saturated fatty acid (A), its derivative, and a triglyceride including the saturated fatty acid (A) as a main constituent fatty acid is transesterified with a component (II) selected from at least one of a fatty acid corresponding to the saturated fatty acid (B), its derivative, and a triglyceride including the saturated fatty acid (B) as a main constituent fatty acid to give a fat composition. In the method, at least one of the components (I) and (II) is required to be a triglyceride.

The transesterification may be carried out in accordance with a conventional procedure, and a catalyst used may be a chemical catalyst or an enzyme catalyst. Examples of the chemical catalyst include sodium methylate and sodium hydroxide. The enzyme catalyst is a lipase that is an enzyme derived from microorganisms. The lipase used in the present invention may have regiospecificity or may not have regiospecificity. Examples of the lipase used in the present invention include lipases obtained from genera *Alcaligenes, Aspergillus, Mucor, Penicillium, Candida,* and the like. The transesterification using the lipase may be carried out by a continuous system using a column or by a batch system.

In order to obtain the fat composition having a predetermined ABB content and (ABB/AAB) ratio for achieving the effect as the object of the present invention, the rate of material fats used during the transesterification is preferably adjusted. Alternatively, from the fat composition containing ABB and AAB obtained by the transesterification, AAA, BBB, excess ABB, or excess AAB is removed by, for example, distillation and/or selection of the temperature condition during separation to purify the fat composition, and thus the fat composition having a predetermined ABB content and (ABB/AAB) ratio can be obtained.

Examples of the distillation method include short path thin film distillation and molecular distillation. The separation method is not specifically limited, and may be a separation method using an organic solvent such as acetone and hexane or a separation method without using any solvent.

The modifying agent for a plastic fat of the present invention is used for the production of a plastic fat. In order to impart the suppressive effect on the physical property changes such as the change in hardness and the formation of coarse crystals and the air containing properties to the plastic. fat, the modifying agent is preferably included so that the ABB content will be 2 to 10% by weight based on the whole plastic fat. The plastic fat of the present invention preferably includes palm oil in an amount of 50 to 98% by weight. The plastic fat preferably includes lauric acid as a constituent fatty acid in a smaller amount. The content of lauric acid in the plastic fat is preferably less than 5% by weight, more preferably less than 1% by weight, and especially preferably 0% by weight, namely, the plastic fat especially preferably includes no lauric acid.

EXAMPLES

Hereinafter, the present invention will be described in further detail with reference to examples, but the present invention is not intended to be limited to the examples. In the examples, "part" and "%" are based on weight unless otherwise specified.

<Measurement of Penetration Value>

The penetration value is a consistency at a measurement temperature represented by a penetration degree. Immediately after the preparation of each shortening in Examples and Comparative Examples, the shortening was stored at 20° C. After one day and 45 days of the storage, each penetration value was determined in accordance with the consistency test in Japanese Industrial Standard K2220-1993 using a digital automatic penetrometer (manufactured by Mitamura Riken Kogyo Inc.) and a standard penetrometer cone (a mass of 102.5 g) in Japanese Industrial Standard.

<Evaluation of Hardness Change of Shortening>

The hardness change of a shortening was evaluated using the difference between the penetration values after one day and 45 days of the storage based on the criteria below.

A: The change in the penetration values during the storage was less than 10.

B: The change in the penetration values during the storage was 10 to 30.

C: The change in the penetration values during the storage was more than 30.

<Evaluation of Creaming Properties of Shortening>

The change in specific gravity over time was determined as follows and evaluated based on the criteria below. Each shortening obtained in Examples and Comparative Examples was controlled to have a temperature of 23° C. so as to have a penetration value of about 150. Using a Hobart mixer (manufactured by Hobart Corporation), 300 g of the shortening was chopped at low speed 1 for 1 minute. Next, 314 g of syrup was added and mixed with the shortening at low speed 1 for 1 minute. Then, the time when the stirring at medium speed 2 was started was regarded as the start, and the specific gravity to water was determined every 1 minute until 5 minutes after the start, every 2.5 minutes until 10 minutes after the start, and every 5 minutes until 30 minutes after the start. The stirring was stopped at every measurement time, an air-containing fat was placed in a 27.3-ml container, the excess fat over the container was leveled off with a spatula, and the fat with the container was weighed. From the weighed result, the container weight was subtracted to give the weight of the fat in the container, and the specific gravity was calculated from the fat weight. The creaming properties were evaluated based on the time until the specific gravity reached the lowest value.

A: The specific gravity reached 0.6 within 10 minutes.
B: The specific gravity reached 0.6 within 30 minutes.

<Evaluation of Emulsification of Shortening>

Each shortening obtained in Examples and Comparative Examples was controlled to have a temperature of 23° C. so as to have a penetration value of about 150. Using a Hobart mixer (manufactured by Hobart Corporation), 300 g of the shortening was chopped at low speed 1 for 1 minute. Next, 314 g of syrup was added and mixed with the shortening at low speed 1 for 1 minute. Then, the stirring at medium speed 2 was started, and stopped after 30 minutes. The degree of separation of the syrup was visually evaluated. The criteria for the evaluation were as follows.

A: The syrup was not separated.
B: The syrup was separated.
C: The syrup was remarkably separated.

Example 1

Preparation of Modifying Agent for Plastic Fat

A modifying agent for a plastic fat as a fat composition composed of a mixture of an ABB type triglyceride as $A_{C16\ to\ C22}B_{C8}B_{C8}$ in which A was stearic acid (C18), palmitic acid (C16), arachidic acid (C20), or behenic acid (C22) and B was caprylic acid (C8) and an AAB type triglyceride as $A_{C16\ to\ C22}A_{C16\ to\ C22}B_{C8}$ in which A was stearic acid (C18), palmitic acid (C16), arachidic acid (C20), or behenic acid (C22) and B was caprylic acid (C8) was prepared as follows.

To 70 parts of extremely hardened canola oil (stearic acid 92%, palmitic acid 5%, arachidic acid 2%, behenic acid 1% or less), 30 parts of MCT (medium chain fatty acid triglyceride, "Actor M2" manufactured by Riken Vitamin Co., Ltd., caprylic acid (melting point 16.5° C.): 99.8% (actual measured value)) was mixed, and the mixture was dehydrated at 90° C. under vacuum. Next, 0.3 part of sodium methylate was added and random transesterification was carried out at 90° C. under vacuum for 30 minutes. Water was added to stop the reaction, and then the reaction mixture was washed with water. Next, 3 parts of activated clay was added, and the whole was stirred under reduced pressure. After 20 minutes, the whole was filtered. Then, to 100 parts of the fat composition as the filtrate, 200 parts of hexane was added, and separation was carried out at 5° C. to remove a high-melting component (63 parts) which is rich in $A_{C16\ to\ C22}A_{C16\ to\ C22}A_{C16\ to\ C22}$. Then, hexane was removed by distillation to give a fat composition (37 parts) having an $A_{C16\ to\ C22}B_{C8}B_{C8}$ content of 54.6% and an $A_{C16\ to\ C22}A_{C16\ to\ C22}B_{C8}$ content of 21.8% based on the whole fat composition. The obtained fat composition had an $A_{C18}B_{C8}B_{C8}$ content of 49.9% and an $A_{C18}A_{C18}B_{C8}$ content of 13.0% based on the whole fat composition.

Example 2

Preparation of Modifying Agent for Plastic Fat

A modifying agent for a plastic fat as a fat composition composed of a mixture of an ABB type triglyceride as $A_{C18}B_{C8}B_{C8}$ in which A was stearic acid (C18) and B was caprylic acid (C8) and an AAB type, triglyceride as $A_{C18}A_{C18}B_{C8}$ in which A was stearic acid (C18) and B was caprylic acid (C8) was prepared as follows.

To 100 parts of MCT (medium chain fatty acid triglyceride, "Actor M2" manufactured by Riken Vitamin Co., Ltd., caprylic acid (melting point 16.5° C.): 99.8% (actual measured value)), 50 parts of ethyl stearate (manufactured by TOKYO CHEMICAL INDUSTRY CO., LTD.) was mixed. To the mixture, 10 parts of 1,3-position specific enzyme, Lipozyme RMIM (manufactured by Novozymes), was added to carry out 1,3-position specific transesterification at 50° C. for 8 hours. After the reaction, unreacted stearic acid and MCT, and caprylic acid as the reaction product were removed by evaporation with a thin film evaporator (210° C., 1 Pa) to give a fat composition (44 parts) having an $A_{C18}B_{C8}B_{C8}$ content of 67.0% and an $A_{C18}A_{C18}B_{C8}$ content of 17.4% based on the whole fat composition, where $A_{C18}B_{C8}B_{C8}$ included stearic acid at the 1-position or the 3-position and $A_{C18}A_{C18}B_{C8}$ included caprylic acid at the 2-position.

Example 3

Preparation of Modifying Agent for Plastic Fat

A modifying agent for a plastic fat as a fat composition composed of a mixture of an ABB type triglyceride as $A_{C16\ to\ C22}B_{C8}B_{C8}$ in which A was stearic acid (C18), palmitic acid (C16), arachidic acid (C20), or behenic acid (C22) and B was caprylic acid (C8), and an AAB type triglyceride as $A_{C16\ to\ C22}A_{C16\ to\ C22}B_{C8}$ in which A was stearic acid (C18), palmitic acid (C16), arachidic acid (C20), or behenic acid (C22) and B was caprylic acid (C8) was prepared as follows.

To 100 parts of extremely hardened canola oil, 65 parts of caprylic acid (manufactured by TOKYO CHEMICAL INDUSTRY CO., LTD.) and 100 parts of hexane were mixed. To the mixture, 10 parts of Lipozyme RMIM was added to carry out 1,3-position specific transesterification at 50° C. for 8 hours, and hexane was removed by distillation. Then, unreacted caprylic acid and fatty acids as the reaction products were removed by evaporation through thin film distillation (180° C., 1 Pa) to give a fat composition (87 parts) having an $A_{C16\ to\ C22}B_{C8}B_{C8}$ content of 20.5%, an $A_{C16\ to\ C22}A_{C16\ to\ C22}B_{C8}$ content of 40.8%, and an $A_{C16\ to\ C22}A_{C16\ to\ C22}A_{C16\ to\ C22}$ content of 21.7% based on the whole. fat composition, where $A_{C16\ to\ C22}B_{C8}B_{C8}$ included stearic acid, palmitic acid, arachidic acid, or behenic acid at the 2-position and $A_{C16\ to\ C22}A_{C16\ to\ C22}B_{C8}$ included caprylic acid at the 1-position or the 3-position. To 87 parts of the fat composition, 58 parts of caprylic acid and 100 parts of hexane were mixed. To the mixture, 8.7 parts of Lipozyme RMIM was added to carry out 1,3-position specific transesterification at 50° C. for 8 hours, and hexane was removed by distillation. Then, unreacted caprylic acid and fatty acids as the reaction products were removed by evaporation through thin film distillation (180° C., 1 Pa) to give a fat composition (55 parts) having an $A_{C16\ to\ C22}B_{C8}B_{C8}$ content of 43.4%, an $A_{C16\ to\ C22}A_{C16\ to\ C22}B_{C8}$ content of 37.9%, and an $A_{C16\ to\ C22}A_{C16\ to\ C22}A_{C16\ to\ C22}$ content of 8.1%, where $A_{C16\ to\ C22}B_{C8}B_{C8}$ included stearic acid, palmitic acid, arachidic acid, or behenic acid at the 2-position and $A_{C16\ to\ C22}A_{C16\ to\ C22}B_{C8}$ included caprylic acid at the 1-position or the 3-position. To 55 parts of the obtained fat composition, 110 parts of hexane, was added, and separation was carried out at 10° C. to remove a high-melting component (23 parts) which is rich in $A_{C16\ to\ C22}A_{C16\ to\ C22}A_{C16\ to\ C22}$. Then, hexane was removed by distillation to give a fat composition (32 parts) having an $A_{C16\ to\ C22}B_{C8}B_{C8}$ content of 61.0% and an $A_{C16\ to\ C22}A_{C16\ to\ C22}B_{C8}$ content of 25.4% based on the whole fat composition, where $A_{C16\ to\ C22}B_{C8}B_{C8}$ included stearic acid, palmitic acid, arachidic acid, or behenic acid at the 2-position. The obtained fat composition has an $A_{C18}B_8B_{C8}$ content of 58.9% and an $A_{C18}A_{C18}B_{C8}$ content of 19.3% based on the whole fat composition, where $A_{C18}B_{C8}B_{C8}$ included stearic acid at the 2-position and $A_{C18}B_{C8}B_{C8}$ included caprylic acid at the 1-position or the 3-position.

Example 4

Preparation of Modifying Agent for Plastic Fat

A modifying agent for a plastic fat as a fat composition composed of a mixture of an ABB type triglyceride as $A_{C16\ to\ C22}B_{C8}B_{C8}$ in which A was stearic acid (C 18), palmitic acid (C 16), arachidic acid (C20), or behenic acid (C22) and B was caprylic acid (C8) and an AAB type triglyceride as $A_{C16\ to\ C22}A_{C16\ to\ C22}B_{C8}$ in which A was stearic acid (C18), palmitic acid (C16), arachidic acid (C20), or behenic acid (C22) and B was caprylic acid (C8) was prepared as follows.

To 70 parts of extremely hardened canola oil, 30 parts of MCT ("Actor M2" manufactured by Riken Vitamin Co., Ltd., caprylic acid (melting point 16.5° C.): 99.8% (actual measured value)) and 100 parts of hexane were mixed. To the mixture, 10 parts of Lipozyme TLIM (manufactured by Novozymes) was added to carry out 1,3-position specific transesterification at 50° C. for 8 hours, and hexane was removed by distillation. The obtained transesterified fat was subjected to thin film distillation (230° C., 1 Pa) to remove a fat composition (9 parts) mainly composed of $B_{C8}B_{C8}B_{C8}$. Furthermore, the obtained fat composition (91 parts) was subjected to thin film distillation (270° C., 1 Pa) to give a fat composition (27 parts) mainly composed of $A_{C16\ to\ C22}B_{C8}B_{C8}$ and a fat composition (64 parts) mainly composed of $A_{C16\ to\ C22}A_{C16\ to\ C22}B_{C8}$. To 27 parts of the obtained fat composition mainly composed of $A_{C16\ to\ C22}B_{C8}B_{C8}$, 54 parts of hexane was added, and separation was carried out at 5° C. to remove some (7 parts) of $A_{C16\ to\ C22}A_{C16\ to\ C22}B_{C8}$. Then, hexane was removed by distillation to give a fat composition (20 parts) having an $A_{C16\ to\ C22}B_{C8}B_{C8}$ content of 81.1% and an $A_{C16\ to\ C22}A_{C16\ to\ C22}B_{C8}$ content of 9.6% based on the whole fat composition. The obtained fat composition had an $A_{C18}B_{C8}B_{C8}$ content of 75.8% and an $A_{C18}A_{C18}B_{C8}$ content of 6.2% based on the whole fat composition.

Example 5

Preparation of Modifying Agent for Plastic Fat

A modifying agent for a plastic fat as a fat composition composed of a mixture of an ABB type triglyceride as $A_{C16\ to\ C22}B_{C8\ to\ C10}B_{C8\ to\ C10}$ in which A is stearic acid (C18), palmitic acid (C16), arachidic acid (C20), or behenic acid (C22) and B was caprylic acid (C8) or capric acid (C10) and an AAB type triglyceride as $A_{C16\ to\ C22}A_{C16\ to\ C22}B_{C8\ to\ C10}$ in which A is stearic acid (C18), palmitic acid (C16), arachidic acid (C20), or behenic acid (C22) and B was caprylic acid (C8) or capric acid (C10) was prepared as follows.

To 30 parts of extremely hardened canola oil, 70 parts of MCT (medium chain fatty acid triglyceride, manufactured by Danisco, caprylic acid 85%, capric acid 15%) was mixed, and the mixture was treated in the same manner as in Example 1 to give a transesterified fat having a $B_{C8\ to\ C10}B_{C8\ to\ C10}B_{C8\ to\ C10}$ content of 45.0%, an $A_{C16\ to\ C22}B_{C8\ to\ C10}B_{C8\ to\ C10}$ content of 41.3%, an $A_{C16\ to\ C22}A_{C16\ to\ C22}B_{C8\ to\ C10}$ content of 10.7%, and an $A_{C16\ to\ C22}A_{C16\ to\ C22}A_{C16\ to\ C22}$ content of 0.7%. The obtained transesterified fat was subjected to thin film distillation (210° C., 0.3 Pa) to remove a fat composition (50 parts) having a $B_{C8\ to\ C10}B_{C8\ to\ C10}B_{C8\ to\ C10}$ content of 84.6%, an $A_{C16\ to\ C22}B_{C8\ to\ C10}B_{C8\ to\ C10}$ content of 12.7%, and an $A_{C16\ to\ C22}A_{C16\ to\ C22}B_{C8\ to\ C10}$ content of 0.1% to give a fat composition (50 parts) having a $B_{C8\ to\ C10}B_{C8\ to\ C10}B_{C8\ to\ C10}$ content of 5.1%, an $A_{C16\ to\ C22}B_{C8\ to\ C10}B_{C8\ to\ C10}$ content of 70.4%, an $A_{C16\ to\ C22}A_{C16\ to\ C22}B_{C8\ to\ C10}$ content of 22.4%, and an $A_{C16\ to\ C22}A_{C16\ to\ C22}A_{C16\ to\ C22}$ content of 1.5% based on the whole fat composition. The obtained fat composition had an $A_{C18}B_{C8\ to\ 10}B_{C8\ to\ 10}$ content of 68.1% and an $A_{C18}A_{C18}B_{C8\ to\ 10}$ content of 20.3% based on the whole fat composition.

Example 6

Preparation of Modifying Agent for Plastic Fat

A modifying agent for a plastic fat as a fat composition composed of a mixture of an ABB type triglyceride as $A_{C16\ to\ C22}B_{C8\ to\ C10}B_{C8\ to\ C10}$ in which A is stearic acid (C18), palmitic acid (C16), arachidic acid (C20), or behenic acid (C22) and B was caprylic acid (C8) or capric acid (C10) and an AAB type triglyceride as $A_{C16\ to\ C22}A_{C16\ to\ C22}B_{C8\ to\ C10}$ in which A is stearic acid (C18), palmitic acid (C16), arachidic acid (C20), or behenic acid (C22) and B was caprylic acid (C8) or capric acid (C10) was prepared as follows.

To 30 parts of extremely hardened canola oil, 70 parts of MCT (medium chain fatty acid triglyceride, "Actor M1" manufactured by Riken Vitamin Co., Ltd., caprylic acid 60%, capric acid 40%) was mixed, and the mixture was treated in the same manner as in Example 1 to give a. transesterified fat having a $B_{C8\ to\ C10}B_{C8\ to\ C10}B_{C8\ to\ C10}$ content of 44.0%, an $A_{C16\ to\ C22}B_{C8\ to\ C10}B_{C8\ to\ C10}$ content of 40.2%, an $A_{C16\ to\ C22}A_{C16\ to\ C22}B_{C8\ to\ C10}$ content of 11.1%, and an $A_{C16\ to\ C22}A_{C16\ to\ C22}A_{C16\ to\ C22}$ content of 1.1% based on the whole transesterified fat. The obtained transesterified fat was subjected to thin film distillation (220° C., 0.3 Pa) to remove a fat composition (52 parts) having a $B_{C8\ to\ C10}B_{C8\ to\ C10}B_{C8\ to\ C10}$ content of 80.5%, an $A_{C16\ to\ C22}B_{C8\ to\ C10}B_{C8\ to\ C10}$ content of 15.0%, and an $A_{C16\ to\ C22}A_{C16\ to\ C22}B_{C8\ to\ C10}$ content of 0.5% to give a fat composition (48 parts) having a $B_{C8\ to\ C10}B_{C8\ to\ C10}B_{C8\ to\ C10}$ content of 5.6%, an $A_{C16\ to\ C22}B_{C8\ to\ C10}B_{C8\ to\ C10}$ content of 67.4%, an $A_{C16\ to\ C22}A_{C16\ to\ C22}B_{C8\ to\ C10}$ content of 22.9%, and an $A_{C16\ to\ C22}A_{C16\ to\ C22}A_{C16\ to\ C22}$ content of 2.1% based on the whole fat composition. The obtained fat composition had an $A_{C18}B_{C8\ to\ C10}B_{C8\ to\ C10}$ content of 66.5% and an $A_{C18}A_{C18}B_{C8\ to\ 10}$ content of 21.3% based on the whole fat composition.

Example 7

Preparation of Modifying Agent for Plastic Fat

A modifying agent for a plastic fat as a fat composition composed of a mixture of an ABB type triglyceride as $A_{C16\ to\ C22}B_{C8}B_{C8}$ in which A was stearic acid (C18), palmitic acid (C16), arachidic acid (C20), or behenic acid (C22) and B was caprylic acid (C8) and an AAB type triglyceride as $A_{C16\ to\ C22}A_{C16\ to\ C22}B_{C8}$ in which A is stearic acid (C18), palmitic acid (C16), arachidic acid (C20), or behenic acid (C22) and B was caprylic acid (C8) was prepared as follows.

To 30 parts of extremely hardened palm stearin oil (palmitic acid 60%, stearic acid 38%, arachidic acid 1% or less, behenic acid less than 0.1%), 70 parts of MCT (medium chain fatty acid triglyceride, "Actor M2" manufactured by Riken Vitamin Co., Ltd., caprylic acid (melting point 16.5° C.): 99.8% (actual measured value)) was mixed, and the mixture was treated in the same manner as in Example 1 to give a transesterified fat having a $B_{C8}B_{C8}B_{C8}$ content of 42.4%, an $A_{C16\ to\ C22}B_{C8}B_{C8}$ content of 40.1%, an $A_{C16\ to\ C22}A_{C16\ to\ C22}B_{C8}$ content of 11.0%, and an $A_{C16\ to\ C22}A_{C16\ to\ C22}A_{C16\ to}$ $C_{22}$ content of 1.1%. The obtained transesterified fat was subjected to thin film distillation (200° C., 0.3 Pa) to remove a fat composition (48 parts) having a $B_{C8}B_{C8}B_{C8}$ content of 82.2%, an $A_{C16\ to\ C22}B_{C8}B_{C8}$ content of 10.2%, and an $A_{C16\ to\ C22}A_{C16\ to\ C22}B_{C8}$ content of 0.3% to give a fat composition (52 parts) having a $B_{C8}B_{C8}B_{C8}$ content of 5.5%, an $A_{C16\ to\ C22}B_{C8}B_{C8}$ content of 65.5%, an $A_{C16\ to\ C22}A_{C16\ to\ C22}B_{C8}$ content of 20.7%, and an $A_{C16\ to\ C22}A_{C16\ to\ C22}A_{C16\ to\ C22}$ content of 2.3% based on the whole fat composition. The obtained fat composition had an $A_{C18}B_{C8}B_{C8}$ content of 26.1% and an $A_{C18}A_{C18}B_{C8}$ content of 3.0% based on the whole fat composition.

Example 8

Preparation of Modifying Agent for Plastic Fat

A modifying agent for a plastic fat as a fat composition composed of a mixture of an ABB type triglyceride as $A_{C16\ to\ C22}B_{C8}B_{C8}$ in which A was stearic acid (C18), palmitic acid (C16), arachidic acid (C20), or behenic acid (C22) and B was caprylic acid (C8) and an AAB type triglyceride as $A_{C16\ to\ C22}A_{C16\ to\ C22}B_{C8}$ in which A is stearic acid (C18), palmitic acid (C16), arachidic acid (C20), or behenic acid (C22) and B was caprylic acid (C8) was prepared as follows.

To 30 parts of extremely hardened high erucic canola oil (behenic acid 49%, stearic acid 39%, arachidic acid 8%, palmitic acid 4%), 70 parts of MCT (medium chain fatty acid triglyceride, "Actor M2" manufactured by Riken Vitamin Co., Ltd., caprylic acid (melting point 16.5° C.): 99.8% (actual measured value)) was mixed, and the mixture was treated in the same manner as in Example 1 to give a transesterified fat having a $B_{C8}B_{C8}B_{C8}$ content of 45.1%, an $A_{C16\ to\ C22}B_{C8}B_{C8}$ content of 40.0%, an $A_{C16\ to\ C22}A_{C16\ to\ C22}B_{C8}$ content of 10.8%, and an $A_{C16\ to\ C22}A_{C16\ to\ C22}A_{C16\ to\ C22}$ content of 0.7%. The obtained transesterified fat was subjected to thin film distillation (200° C., 0.3 Pa) to remove a fat composition (48 parts) having a $B_{C8}B_{C8}B_{C8}$ content of 89.9%, an $A_{C16\ to\ C22}B_{C8}B_{C8}$ content of 4.2%, and an $A_{C16\ to\ C22}A_{C16\ to\ C22}B_{C8}$ content of 0.3% to give a fat composition (52 parts) having a $B_{C8}B_{C8}B_{C8}$ content of 4.0%, an $A_{C16\ to\ C22}B_{C8}B_{C8}$ content of 72.9%, an $A_{C16\ to\ C22}A_{C16\ to\ C22}B_{C8}$ content of 20.3%, and an $A_{C16\ to\ C22}A_{C16\ to\ C22}A_{C16\ to\ C22}$ content of 1.5% based on the whole fat composition. The obtained fat composition had an $A_{C18}B_{C8}B_{C8}$ content of 30.0% and an $A_{C18}A_{C18}B_{C8}$ content of 3.5% based on the whole fat composition.

Comparative Example 1

Preparation of Modifying Agent for Plastic Fat

A modifying agent for a plastic fat as a fat composition composed of a mixture of an ABB type triglyceride as $A_{C16\ to\ C22}B_{C8}B_{C8}$ in which A was stearic acid (C18), palmitic acid (C16), arachidic acid (C20), or behenic acid (C22) and B was caprylic acid (C8) and an AAB type triglyceride as $A_{C16\ to\ C22}A_{C16\ to\ C22}B_{C8}$ in which A is stearic acid (C18), palmitic acid (C16), arachidic acid (C20), or behenic acid (C22) and B was caprylic acid (C8) was prepared as follows.

To 100 parts of the fat as the filtrate obtained in the same manner as in Example 1, 200 parts of hexane was added, and separation was carried out at 20° C. to remove a high-melting component (25 parts) which is rich in $A_{C16\ to\ C22}A_{C16\ to\ C22}$, and hexane was removed by distillation. To 75 parts of the fat composition, 150 parts of hexane was added, and separation was carried out at 5° C. to remove a low-melting component (32 parts) which is rich in $A_{C16\ to\ C20}B_{C8}B_{C8}$. Then, hexane was removed by distillation to give a fat composition (43 parts) having an $A_{C16\ to\ C22}A_{C16\ to\ C22}B_{C8}$ content of 68.7% and an $A_{C16\ to\ C22}B_{C8}B_{C8}$ content of 20.1% based on the whole composition. The obtained fat composition had an $A_{C18}A_{C18}B_{C8}$ content of 60.3% and an $A_{C18}B_{C8}B_{C8}$ content of 18.8% based on the whole fat composition.

Comparative Example 2

Preparation of Modifying Agent for Plastic Fat

A modifying agent for a plastic fat as a fat composition composed of a mixture of an ABB type triglyceride as $A_{C16}B_{C12}B_{C12}$ in which A was palmitic acid (C16) and B was lauric acid (C12) and an AAB type triglyceride as $A_{C16}A_{C16}B_{C12}$ in which A was palmitic acid (C16) and B was lauric acid (C12) was prepared as follows.

To 100 parts of trilaurin (manufactured by TOKYO CHEMICAL INDUSTRY CO., LTD.) (melting point of lauric acid: 43.5° C.), 100 parts of palmitic acid (melting point: 63.1° C.) (manufactured by Daiwa Pharmaceutical Co., Ltd.) and 100 parts of hexane were mixed. To the mixture, 10 parts of Lipozyme RMIM was added to carry out 1,3-position specific transesterification at 50° C. for 8 hours, and hexane was removed by distillation. Then, unreacted palmitic acid and lauric acid as the reaction product were removed by thin film distillation to give a fat composition (92 parts) having a $B_{C12}B_{C12}B_{C12}$ content of 25.5%, where B was lauric acid, having an $A_{C16}B_{C12}B_{C12}$ content of 46.6%, where A was palmitic acid and B was lauric acid, and having an $A_{C16}B_{C12}A_{C16}$ content of 17.8%. To 92 parts of the fat composition, 184 parts of hexane was added, and separation was carried out at 10° C., and hexane was removed by distillation to give a fat composition (45 parts) having an $A_{C16}B_{C12}B_{C12}$ content of 51.7% and an $A_{C16}B_{C12}A_{C16}$ content of 13.6% based on the whole fat composition.

Examples 9 to 16

Preparation of Shortening (Plastic Fat)

Five parts of each modifying agent for a plastic fat obtained in Examples 1 to 8 and 95 parts of palm oil were melted and mixed, and the mixture was kneaded while rapidly cooled using a rapid-cooling kneader to prepare a shortening.

Comparative Example 3

Preparation of Shortening (Plastic Fat)

A shortening having a palm oil content of 100% was prepared in the same manner as in Examples 9 to 16 without adding the modifying agent.

Comparative Example 4

Preparation of Shortening (Plastic Fat)

Two parts of the modifying agent for a plastic fat prepared in Example 4 and 98 parts of palm oil were melted and mixed to prepare a shortening in the same manner as in Examples 9 to 16.

Comparative Example 5

Preparation of Shortening (Plastic Fat)

Five parts of the modifying agent for a plastic fat obtained in Comparative Example 1 and 95 parts of palm oil were melted and mixed to prepare a shortening in the same manner as in Examples 9 to 16.

Comparative Example 6

Preparation of Shortening (Plastic Fat)

Five parts of the modifying agent for a plastic fat obtained in Comparative Example 2 and 95 parts of palm oil were melted and mixed to prepare a shortening in the same manner as in Examples 9 to 16.

The penetration value (hardness) of each shortening obtained in Examples 9 to 16 and Comparative Examples 3 to 6 was determined with time. The creaming properties and emulsifying properties were also evaluated. These results are summarized in Table 1.

change in the hardness over time. However, a shortening having a larger ABB/AAB value had a higher hardness than that of a shortening having a smaller ABB/AAB value. In contrast, the shortening of Comparative Example 3 that was prepared from palm oil alone without adding the modifying agent had a high hardness and a large change over time. The shortening of Comparative Example 4 that included the modifying agent in a small amount and had a small ABB content had a high hardness and a large change over time. The shortening of Comparative Example 5 that had a small ABB content because the fat composition of Comparative. Example 1 having a small ABB/AAB value was added as the modifying agent had a high hardness and a large change over time. The shortening of Comparative Example 6 that included the fat composition of Comparative Example 2 including palmitic acid (C16) as the saturated fatty acid (A) and lauric acid (C12) as the saturated fatty acid (B) in the ABB constituent fatty acids had a high hardness and a large change over time even when the fat composition having a weight ratio (ABB/AAB) of ABB to AAB of 2 or more was included so as to have an ABB content of 2% or more.

TABLE 1

| | | Example 9 | Example 10 | Example 11 | Example 12 | Example 13 | Example 14 |
|---|---|---|---|---|---|---|---|
| Modifying agent for plastic fat used | | Example 1 | Example 2 | Example 3 | Example 4 | Example 5 | Example 6 |
| ABB (% by weight) | | 54.6 | 67.0 | 61.0 | 81.1 | 70.4 | 67.4 |
| AAB (% by weight) | | 21.8 | 17.4 | 25.4 | 9.6 | 22.4 | 22.9 |
| ABB/AAB | | 2.5 | 3.9 | 2.5 | 8.4 | 3.1 | 3.0 |
| $A_{C16-C22}$ (% by weight) | | 58.0 | 60.9 | 65.3 | 58.5 | 58.6 | 58.9 |
| $B_{C6-C10}$ (% by weight) | | 40.9 | 38.6 | 33.8 | 40.8 | 40.4 | 40.4 |
| $A_{C18}$ (% by weight) | | 50.6 | 59.9 | 61.7 | 53.9 | 54.6 | 54.9 |
| $B_{C8-C10}$ (% by weight) | | 40.9 | 38.6 | 33.8 | 40.8 | 40.4 | 40.4 |
| Composition amount in shortening | Modifying agent for plastic fat (parts by weight) | 5 | 5 | 5 | 5 | 5 | 5 |
| | ABB content (% by weight) | 2.7 | 3.4 | 3.1 | 4.1 | 3.4 | 3.4 |
| | AAB content (% by weight) | 1.1 | 0.9 | 1.2 | 0.5 | 1.1 | 1.1 |
| | Lauric acid content (% by weight) | 0 | 0 | 0 | 0 | 0 | 0 |
| | Palm oil (parts by weight) | 95 | 95 | 95 | 95 | 95 | 95 |
| Physical property evaluation | Penetration value after 1 day | 159 | 123 | 112 | 109 | 143 | 128 |
| | Penetration value after 45 days | 148 | 120 | 117 | 102 | 142 | 123 |
| | Change in hardness | B | A | A | A | A | A |
| | Creaming properties | A | A | A | A | A | A |
| | Emulsifying properties | A | A | A | A | A | A |

| | | Example 15 | Example 16 | Comparative Example 3 | Comparative Example 4 | Comparative Example 5 | Comparative Example 6 |
|---|---|---|---|---|---|---|---|
| Modifying agent for plastic fat used | | Example 7 | Example 8 | — | Example 4 | Comparative Example 1 | Comparative Example 2 |
| ABB (% by weight) | | 65.5 | 72.9 | | 81.1 | 20.1 | 51.7 |
| AAB (% by weight) | | 20.7 | 20.3 | | 9.6 | 68.7 | 13.6 |
| ABB/AAB | | 3.2 | 3.6 | | 8.4 | 0.3 | 3.8 |
| $A_{C16-C22}$ (% by weight) | | 59.4 | 62.8 | | 58.5 | 84.7 | 35.3 |
| $B_{C6-C10}$ (% by weight) | | 39.3 | 36.6 | | 40.8 | 14.8 | — |
| $A_{C18}$ (% by weight) | | 24.3 | 24.0 | | 53.9 | 79.5 | — |
| $B_{C8-C10}$ (% by weight) | | 39.3 | 36.6 | | 40.8 | 14.8 | — |
| Composition amount in shortening | Modifying agent for plastic fat (parts by weight) | 5 | 5 | 5 | 2 | 5 | 5 |
| | ABB content (% by weight) | 3.3 | 3.6 | — | 1.6 | 1.0 | 2.5 |
| | AAB content (% by weight) | 1.0 | 1.0 | — | 0.2 | 3.4 | 0.7 |
| | Lauric acid content (% by weight) | 0 | 0 | 0 | 0 | 0 | 64 |
| | Palm oil (parts by weight) | 95 | 95 | 100 | 98 | 95 | 95 |
| Physical property evaluation | Penetration value after 1 day | 161 | 135 | 132 | 121 | 148 | 152 |
| | Penetration value after 45 days | 149 | 113 | 81 | 73 | 86 | 92 |
| | Change in hardness | B | B | C | C | C | C |
| | Creaming properties | A | A | B | B | B | A |
| | Emulsifying properties | A | A | C | B | B | B |

As shown in Table 1, each shortening of Examples 9 to 16 that included, as the modifying agent, the fat composition having a weight ratio (ABB/AAB) of ABB to AAB of 2 or more so as to have an ABB content of 2% or more had a small As for the creaming properties and emulsifying properties of the obtained shortenings, the shortening that included the modifying agent composed of the fat composition including ABB in which the saturated fatty acid (A) was C16 to C22 and the saturated fatty acid (B) was C8 and C10, or including ABB in which the saturated fatty acid (A) was C16 and the saturated fatty acid (B) was C12, and having a weight ratio (ABB/AAB) of ABB to AAB of 2 or more, and that had an ABB content of 2% or more obtained higher creaming properties than those of the shortening prepared from palm oil alone. As for the emulsifying properties, the shortening that included the modifying agent composed of the fat composition including ABB in which the saturated fatty acid (A) was C 16 to C22 and the saturated fatty acid (B) of C8 and C10, and having a weight ratio (ABB/AAB) of ABB to AAB of 2 or more, and that had an ABB content of 2% or more did not cause syrup separation.

The invention claimed is:

1. A plastic fat comprising:
a modifying agent for the plastic fat comprising a fat composition including a triglyceride containing a saturated fatty acid (A) having a melting point of 60° C. or more and a saturated fatty acid (B) having a melting point of 40° C. or less as constituent fatty acids,
the fat composition containing an ABB type triglyceride bonded with one saturated fatty acid (A) and two saturated fatty acids (B) in an amount of 40 to 85% by weight based on the whole fat composition, and having a weight ratio (ABB/AAB) of the ABB type triglyceride to an AAB type triglyceride bonded with two saturated fatty acids (A) and one saturated fatty acid (B) of 2 to 15,
said modifying agent containing the ABB type triglyceride of 2 to 10% by weight based on the whole plastic fat;
palm oil of 50 to 98% by weight; and
lauric acid of less than 5% by weight.

2. A plastic fat comprising:
a modifying agent for the plastic fat comprising a fat composition including a triglyceride containing a saturated fatty acid (A) having a melting point of 60° C. or more and a saturated fatty acid (B) having a melting point of 40° C. or less as constituent fatty acids,
the fat composition containing an ABB type triglyceride bonded with one saturated fatty acid (A) and two saturated fatty acids (B) in an amount of 40 to 85% by weight based on the whole fat composition, and having a weight ratio (ABB/AAB) of the ABB type triglyceride to an AAB type triglyceride bonded with two saturated fatty acids (A) and one saturated fatty acid (B) of 2 to 15,
wherein a C16 to C22 saturated fatty acid (A) is included in an amount of 50 to 70% by weight and a C6 to C10 saturated fatty acid (B) is included in an amount of 30 to 50% by weight based on the whole fatty acids constituting the triglyceride,
said modifying agent containing the ABB type triglyceride of 2 to 10% by weight based on the whole plastic fat;
palm oil of 50 to 98% by weight; and
lauric acid of less than 5% by weight.

3. A plastic fat comprising:
a modifying agent for the plastic fat comprising a fat composition including a triglyceride containing a saturated fatty acid (A) having a melting point of 60° C. or more and a saturated fatty acid (B) having a melting point of 40° C. or less as constituent fatty acids,
the fat composition containing an ABB type triglyceride bonded with one saturated fatty acid (A) and two saturated fatty acids (B) in an amount of 40 to 85% by weight based on the whole fat composition, and having a weight ratio (ABB/AAB) of the ABB type triglyceride to an AAB type triglyceride bonded with two saturated fatty acids (A) and one saturated fatty acid (B) of 2 to 15,
wherein a C18 saturated fatty acid (A) is included in an amount of 50 to 70% by weight and a C8 to C10 saturated fatty acid (B) is included in an amount of 30 to 50% by weight based on the whole fatty acids constituting the triglyceride,
said modifying agent containing the ABB type triglyceride of 2 to 10% by weight based on the whole plastic fat;
palm oil of 50 to 98% by weight; and
lauric acid of less than 5% by weight.

* * * * *